(12) United States Patent
Bailey

(10) Patent No.: US 7,104,992 B2
(45) Date of Patent: Sep. 12, 2006

(54) SPINAL FIXATION SYSTEM

(75) Inventor: Kirk J Bailey, Blairstown, NJ (US)

(73) Assignee: EBI, L.P., Parsippany, NJ (US)

(*) Notice: Subject to any disclaimer, the term of this patent is extended or adjusted under 35 U.S.C. 154(b) by 550 days.

(21) Appl. No.: 10/341,658

(22) Filed: Jan. 14, 2003

(65) Prior Publication Data

US 2004/0138661 A1    Jul. 15, 2004

(51) Int. Cl.
*A61B 17/70*   (2006.01)

(52) U.S. Cl. .................... 606/61; 606/60; 606/72; 606/73

(58) Field of Classification Search ............ 606/60, 606/61, 72, 73
See application file for complete search history.

(56) References Cited

U.S. PATENT DOCUMENTS

| | | | |
|---|---|---|---|
| 5,176,680 A | 1/1993 | Vignaud et al. | 606/61 |
| 5,486,174 A | 1/1996 | Fournet-Fayard et al. | 606/61 |
| 5,501,684 A * | 3/1996 | Schlapfer et al. | 606/73 |
| 5,507,746 A | 4/1996 | Lin | 606/61 |
| 5,531,745 A | 7/1996 | Ray | 606/61 |
| 5,569,247 A | 10/1996 | Morrison | 606/61 |
| 5,575,791 A | 11/1996 | Lin | 606/61 |
| 5,702,394 A | 12/1997 | Henry et al. | 606/61 |
| 5,716,357 A | 2/1998 | Rogozinski | 606/61 |
| 5,725,527 A | 3/1998 | Biedermann et al. | |
| 5,735,852 A | 4/1998 | Amrein et al. | 606/61 |
| 5,810,817 A | 9/1998 | Roussouly et al. | |
| 5,876,403 A | 3/1999 | Shitoto | 606/61 |
| 5,910,142 A | 6/1999 | Tatar | 606/61 |
| 5,938,663 A * | 8/1999 | Petreto | 606/61 |
| 5,947,965 A | 9/1999 | Bryan | |
| 5,984,924 A | 11/1999 | Asher et al. | 606/61 |
| 6,001,102 A | 12/1999 | Barbera Alacreu | 606/73 |
| 6,004,322 A | 12/1999 | Bernstein | 606/61 |
| 6,010,504 A | 1/2000 | Rogozinski | 606/61 |
| 6,022,350 A | 2/2000 | Ganem | 606/61 |
| 6,030,388 A | 2/2000 | Yoshimi et al. | 606/61 |

(Continued)

FOREIGN PATENT DOCUMENTS

| | | |
|---|---|---|
| EP | 0846444 | 6/1998 |
| EP | 0923908 | 6/1999 |
| EP | 1454593 | 9/2004 |
| WO | 01/58369 | 8/2001 |

*Primary Examiner*—Thomas Barrett
*Assistant Examiner*—David A. Izquierdo
(74) *Attorney, Agent, or Firm*—Harness, Dickey & Pierce, P.L.C.

(57) ABSTRACT

A spinal fixation system includes a rod, an anchor, and a clamp assembly. The anchor is adapted to engage a bone. The clamp assembly secures the anchor to the rod. The clamp assembly includes a first portion with first and second flanges for receiving the anchor. A compressible ball is carried by the second portion of the clamp assembly. The ball has a through hole receiving the rod. The through hole is defined by a generally cylindrical inner surface having at least one relieved channel. The first and second flanges include first and second opposing surfaces, respectively. The first and second opposing surfaces are normally angled relative to one another. A nut which threadably engages an upper shaft of the fastener is tightened to draw together the first and second flanges to a position in which they are generally parallel to one another. At least a portion of the through hole tapers from one of the first and second ends towards a center of the ball.

10 Claims, 3 Drawing Sheets

U.S. PATENT DOCUMENTS

| | | | |
|---|---|---|---|
| 6,053,917 A | 4/2000 | Sherman et al. | 606/61 |
| 6,123,706 A | 9/2000 | Lange | 606/61 |
| 6,299,614 B1 | 10/2001 | Kretschmer et al. | 606/61 |
| 6,352,537 B1 | 3/2002 | Strnad | 606/61 |
| 6,626,906 B1 | 9/2003 | Young | |
| 2001/0034521 A1 | 10/2001 | Bailey et al. | |

* cited by examiner

SPINAL FIXATION SYSTEM

FIELD OF THE INVENTION

The present invention relates generally to the field of spinal fixation devices. More specifically, the present invention is directed to a clamp assembly of a spinal fixation system that couples a rod and a bone anchor.

BACKGROUND OF THE INVENTION

The spinal column is a highly complex structure which houses and protects critical elements of the nervous system. In spite of these complexities, the spinal column is a highly flexible structure, capable of a high degree of curvature and twist through a wide range motion. Genetic or developmental irregularities, trauma, chronic stress, tumors, and disease, however, can result in spinal pathologies which either limit this range of motion, or threaten the critical elements of the nervous system housed within the spinal column.

A variety of systems has been disclosed in the art which achieve immobilization of portions of the spinal column by implanting artificial assemblies in or on the spinal column. These assemblies may be generally classified as anterior, posterior or lateral implants. Posterior implants are attached to the back of the spinal column generally by coupling to the pedicles with screws, or through hooks that attach under the lamina. In either case, the implants generally include elongate support rod elements which are coupled to the screws or hooks to immobilize two or more sequential vertebrae, for example to hold them stable so that adjacent bones may be fused with bone graft.

During implantation of a spinal fixation system of the type having an elongated support rod and anchors, it is important to provide adjustability between the support rod and the anchors. Adjustability facilitates ideal placement of the bone anchors relative to the spine. Preferably, the adjustability between the support rod and the anchors allows the supports rods to translate relative to the anchors and also allows for pivotal movement of the anchors relative to the support rod. The spinal system must also be able to arrest relative movement between the support rod and the anchors after implantation so that the spinal segments are post-operatively immobilized.

While known spinal fixation systems have proven to be useful for various applications, they are all associated with drawbacks. In this regard, the fixation screws or hooks of most known systems are difficult or impossible to adequately tighten to arrest relative movement between the anchors and support rod after implantation. Overcoming this limitation typically involves a complex clamping arrangement or an arrangement that requires undue tightening. Use of known systems are often a tedious process, which is inconsistent in result and adds unwanted time to a procedure.

Accordingly, it remains a need in the art to provide an improved spinal system clamping mechanism for coupling a rod and a bone anchor that overcomes the above discussed and other drawbacks of the prior art.

SUMMARY OF THE INVENTION

According to one aspect, the present invention relates to a system for spinal fixation which includes an improved clamp assembly for securing an anchor to a rod.

It is an object of the present invention to provide a clamp assembly for a spinal fixation system that selectively permits relative translation and rotation between an anchor and a rod.

It is another object of the present invention to provide a locking ball design for a spinal fixation clamp assembly that allows for more uniform collapse and thereby increases locking strength independent of the position of the ball.

It is another object of the present invention to provide a ball of a spinal clamp assembly that does not impinge on a contoured rod.

In one form, the present invention provides a spinal fixation system including a rod, an anchor, and a clamp assembly. The anchor is adapted to engage a bone. The clamp assembly secures the anchor to the rod. The clamp assembly includes a first portion for receiving the anchor. A compressible ball is carried by the second portion of the clamp assembly. The ball has a through hole receiving the rod. The through hole is defined by a generally cylindrical inner surface having at least one relieved channel.

In another form, the present invention provides a clamp assembly for securing a bone anchor to a generally cylindrical rod. The clamp assembly includes first and second spaced apart flanges for receiving a portion of a bone anchor. The first and second flanges include first and second opposing surfaces, respectively. The first and second opposing surfaces are normally angled relative to one another. A nut which threadably engages an upper shaft of the fastener is tightened to draw together the first and second flanges to a position in which they are generally parallel to one another.

In another form, the present invention provides a compressible ball for receiving a generally cylindrical rod of a spinal system. The compressible ball cooperates with a clamp body to form a ball and socket joint. The compressible ball includes a through hole for receiving the rod. The through hole extends along an axis and has a first end and a second end. At least a portion of the through hole tapers from one of the first and second ends towards a center of the ball. Preferably, both ends of the through hole taper and a center portion of the through hole has a constant diameter.

DETAILED DESCRIPTION OF THE PREFERRED EMBODIMENT

Figure 1:
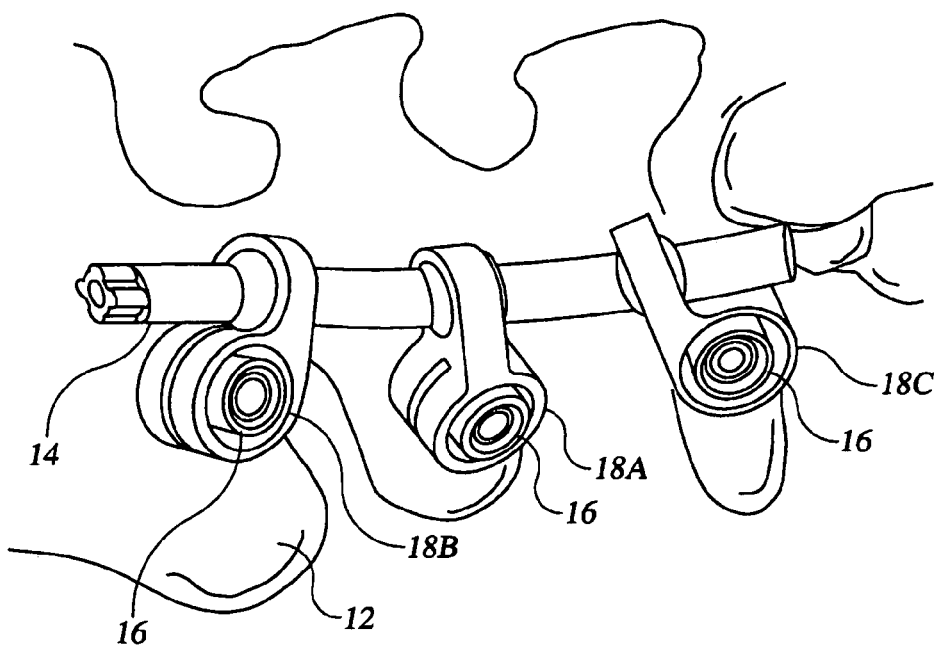
FIG. 1 is a perspective view of a spinal fixation system constructed in accordance with the teachings of a preferred embodiment of the present invention, the spinal fixation system shown arranged in an exemplary construct and operatively attached to a human spinal column.

The following description of the preferred embodiments of the present invention is merely exemplary in nature and is in no way intended to limit the subject invention or its application or uses.

With general reference to the drawings, a spinal fixation system constructed in accordance with the teachings of the preferred embodiment of the present invention is illustrated and generally identified at reference character 10. As shown in the environmental view of FIG. 1, components of the system 10 have been arranged in an exemplary construct for attachment to a portion of a spinal column 12 of a human patient. The components of the system 10 of the present invention used in the construct of FIG. 10 generally include a linkage in the form of a generally cylindrical support rod 14, a plurality of spinal anchors 16 for engaging the spinal column 12, and a plurality of clamp assemblies 18 securing the spinal anchors 16 to the cylindrical rod 14.

The spinal anchors are illustrated throughout the drawings as bone screws 16. Alternatively, it will be understood by those skilled in the art that other types of anchors known in the art may be employed for directly engaging the spine. For example, the anchors may alternatively be hooks that attach under the lamina of the spine.

Figure 2:
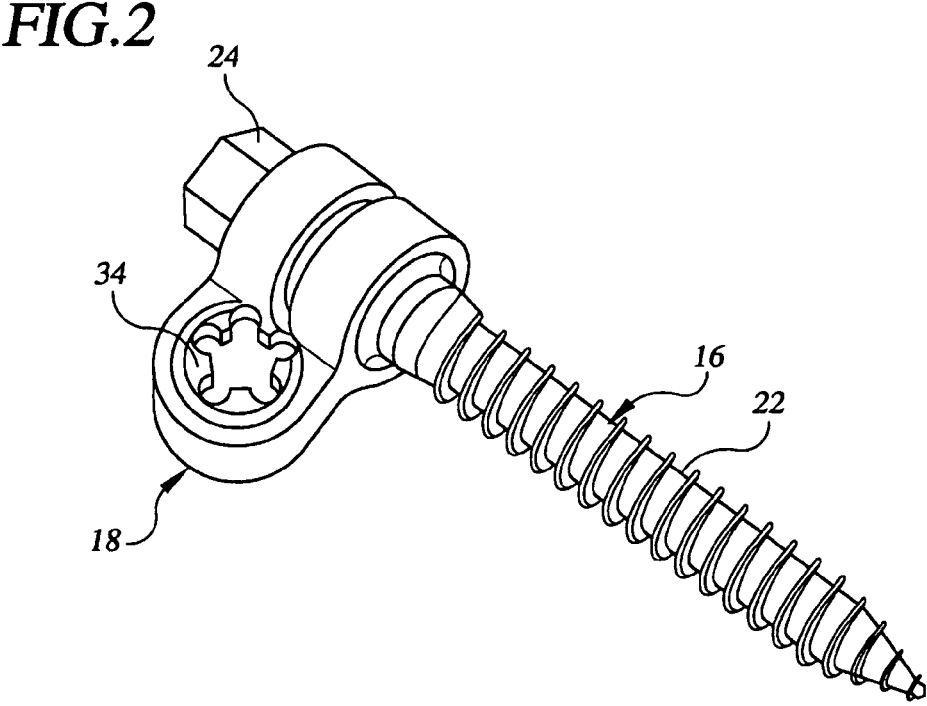
FIG. 2 is a perspective view of one of the spinal anchors and an associated clamp assembly of FIG. 1 removed from the construct of FIG. 1 for purposes of illustration.
Figure 3:
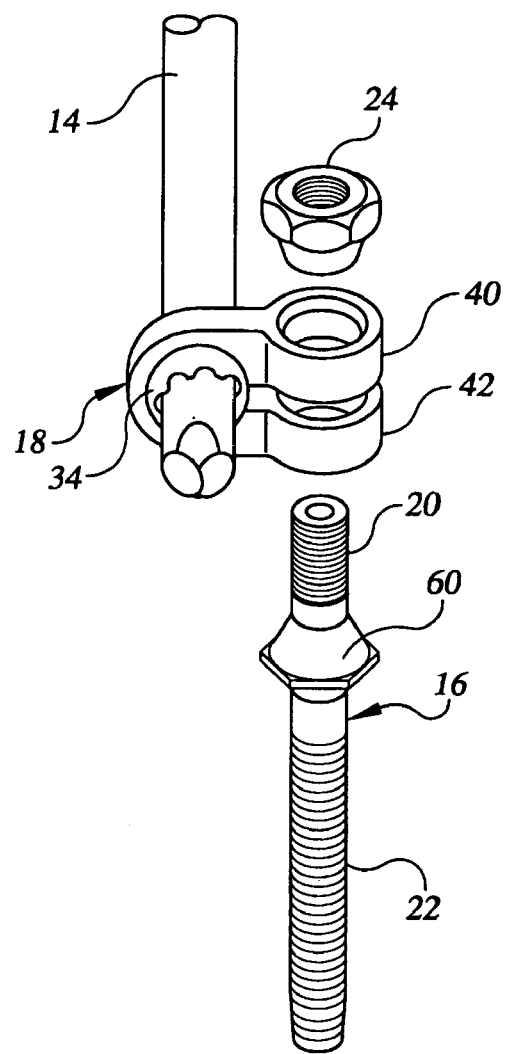
FIG. 3 is a partially exploded side view of a portion of the construct of FIG. 1.
Figure 4:
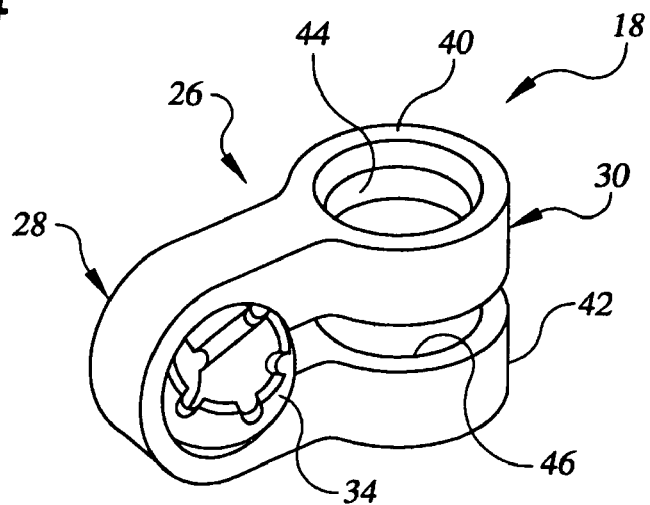
FIG. 4 is a perspective view of the clamp assembly of FIG. 2.

With particular reference to FIGS. 2 and 3, one of the spinal anchors 16 and an associated one of the clamp assemblies 18 are illustrated in further detail. The spinal anchor 16 includes an upper threaded shaft portion 20 and a lower threaded shaft portion 22. The upper threaded shaft portion 20 threadably engages a nut 24 when the spinal anchor 16 is secured to a linkage or rod 14 in a manner discussed below. The rod is preferably a generally cylindrical rod 14.

The clamp assemblies 18 each adjustably interconnect one of the spinal anchors 16 that engage the spinal column 12 with the rod 14. In the exemplary construct of FIG. 1, the system 10 of the present invention is illustrated to include three clamp assemblies 18A, 18B, 18C. A first of the clamp assemblies 18A is shown in further detail in FIGS. 2–6 and is illustrated to generally include a body 26 having a first portion 28 for engaging the rod 14 and a second portion 30 for engaging the spinal anchor 16. The body 26 of the clamp assembly 18A is shown to generally have a C-shape with an intermediate portion or arm that defines an opening 32 for receiving the rod 14. In the embodiment illustrated, the opening 32 is partially spherical and is adapted to adjustably receive a compressible locking member or ball 34.

Figure 5A:
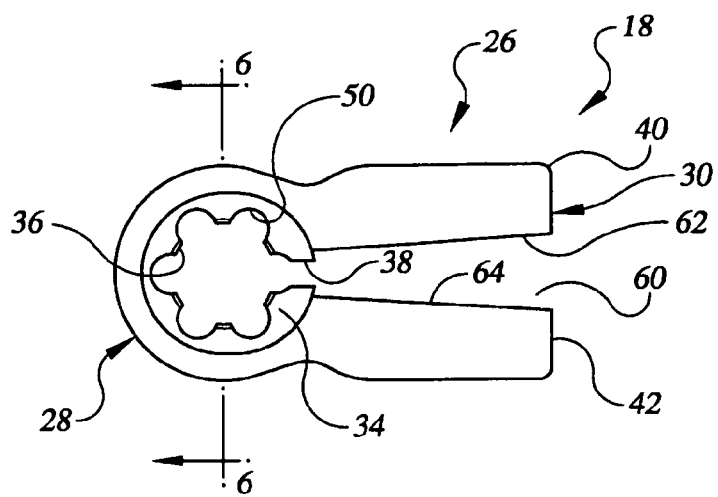
FIG. 5A is a side view of the clamp assembly of FIG. 4 shown with the first and second flanges normally spaced apart.
Figure 5B:
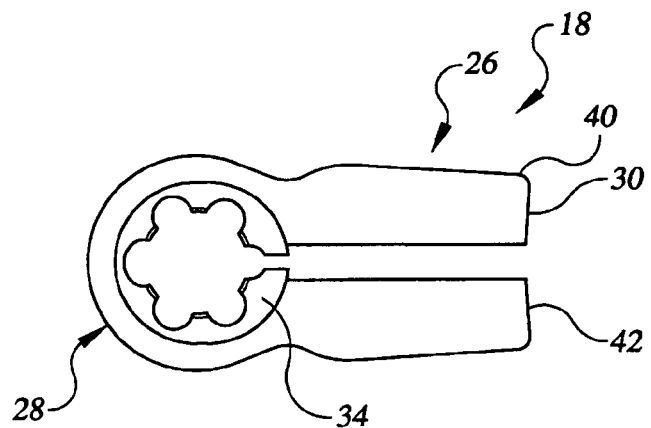
FIG. 5B is a view similar to FIG. 5A illustrating the first and second flanges drawn together.
Figure 6:
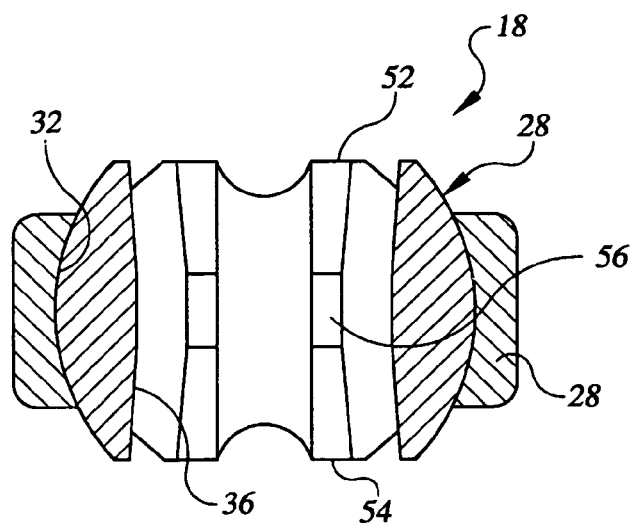
FIG. 6 is a cross-sectional view taken along the line 6—6 of FIG. 5A.

The compressible locking ball 34 is shown particularly in FIGS. 5A and 5B and the cross-sectional views of FIG. 6. As shown, the locking ball 34 is generally spherical in shape and includes an aperture or through hole 36 which passes therethrough for receiving the rod 14. As will become more apparent below, the clamp body 26 and the ball 34 cooperate to form a ball and socket joint that allows pivotal movement of the rod 14 relative to the anchor 16. This pivotal movement is about an imaginary center of the ball 34. The locking ball 34 is normally permitted to universally move within the opening 32. A slit 38 is provided in the locking ball 34 to facilitate compression of the ball and resulting clamping on the rod 14.

The through hole 36 is defined by a generally cylindrical inner surface. The generally cylindrical inner surface preferably includes at least one relieved channel 50. In the embodiment illustrated, the cylindrical inner surface is shown to include five relieved channels 50. The particular number of relieved channels 50 will be understood to be a matter of design choice and may vary from that shown in the drawings. The relieved channels 50 allow for a more uniform collapse of the locking ball 34. In this manner, the locking strength of the clamp assembly 18 is increased independent of the position of the ball 34 within the partially spherical opening defined by the clamp 34.

As perhaps most particularly shown in the cross-section view of FIG. 6, at least a portion of the through hole 36 tapers from a first end 52 of the through hole 36 to a second end 54 of the through hole 36 toward a center of the locking ball 34. As shown, the through hole 36 preferably tapers from the first end 52 towards the center and also from the second end 54 towards the center. A center portion 56 of the through hole 36 has a constant diameter. This configuration of the through hole 36 allows the locking ball 34 to be loaded and not impinge on a contoured rod.

In the embodiment illustrated, the through hole 36 passes through the center of the locking ball 34. Alternatively, the through hole 36 may be eccentric to the sphere defined by the locking ball 34. By orienting the through hole 36 eccentric to the sphere, adjustments can be made by rotating the locking ball 34 within the clamp body 26.

The clamp body 26 further includes a first or upper flange 40 and a second or lower flange 42. In the embodiment illustrated, the upper and lower flanges 40 and 42 are symmetrical about a plane extending therebetween. The upper and lower flanges 40 and 42 are shown to be generally circular in shape. The intermediate portion or arm of the clamp body 26 that extends between the flanges 40 and 42 is disposed radially relative to the upper and lower flanges 40 and 42. The upper and lower flanges 40 and 42 define distinct but aligning apertures 44 and 46 (see FIG. 4), respectively. The apertures 44 and 46 are both associated with recesses 48 to receive either a nut 24 or a partially spherical shaped portion 60 of the screw 16, respectively. In this manner, it is impossible to put the clamp assembly 18 on the rod 14 upside down.

As shown particularly in FIG. 5A, the first and second flanges 40 and 42 are normally spaced apart by a gap. The first and second flanges 40 and 42 includes first and second opposing surfaces 62 and 64, respectively. As shown in FIG. 5A, when the first and second flanges 40 and 42 are normally spaced apart, the opposing surfaces 60 and 64 are angled relative to one another.

Upon tightening of the nut 24, movement of the clamp body 26 relative to the rod 14 is arrested. Explaining further, tightening of the nut 24 serves to draw the upper and lower flanges 40 and 42 together causing the intermediate portion of the clamp body 26 to compress squeeze the locking ball 34 and correspondingly clamp the rod 14. Relative movement is also arrested between the locking ball 34 and the clamp body 26.

Importantly, the clamp body 26 is formed to include sufficient spacing between the upper and lower flanges 40 and 42 so that the gap 60 is always maintained throughout the range of tightening. In this manner, clamping forces are more efficiently transferred to the locking ball 34. The clamp body 26 is illustrated in a fully clamped condition in FIG. 5B. As shown, the opposing surfaces 62 and 64 are oriented generally parallel to one another.

With particular reference to FIG. 1, the clamp assemblies 18B and 18C will be understood to be identical. The clamp assemblies 18B and 18C differ from the clamp assembly 18A in that the second portion 30 is tangentially oriented relative to the first and second flanges 40 and 42. In other words, the intermediate portion or arm that connects the first and second flanges 40 and 42 is offset to one side from a radial position. This offset allows the rod 14 to be positioned closer to the anchor 16 and reduces the medial lateral profile of the construct. Otherwise, it will be understood that the clamp assemblies 18A–18C are identical.

While the invention has been described in the specification and illustrated in the drawings with reference to preferred embodiments, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. A clamp assembly for securing a bone anchor to a generally cylindrical rod, the clamp assembly comprising:
   a first portion for receiving the anchor;
   a second portion having a partially spherical opening; and
   a compressible ball received in the opening of the second portion, the compressible ball having a through hole for receiving the generally cylindrical rod, wherein the compressible ball defines at least one relieved channel on an inner surface of the through hole for collapsing and compressing the generally cylindrical rod.

2. The clamp assembly of claim 1, wherein the compressible ball comprises a plurality of relieved channels defined on the inner surface of the through hole.

3. The clamp assembly of claim 2, wherein the first portion includes first and second spaced apart flanges comprising first and second opposing surfaces, respectively, the first and second opposing surfaces movable between angled and parallel orientations relative to one another.

4. The clamp assembly of claim 1, wherein the through hole extends along an axis and has a first end and a second end, at least a portion of the through hole tapering from one of the first and second ends toward a center portion of the ball.

5. The clamp assembly of claim 4, wherein the through hole tapers from the first end toward the center and from the second end toward the center.

6. The clamp assembly of claim 4, wherein a center portion of the through hole has a constant diameter.

7. The clamp assembly of claim 1, wherein the first portion includes first and second spaced apart flanges comprising first and second opposing surfaces, respectively, the first and second opposing surfaces being angled relative to one another before the first and second flanges are tightened relative to one another.

8. The clamp assembly of claim 1, wherein the clamp assembly is operative to selectively arrest relative movement between the anchor and the rod.

9. The clamp assembly of claim 1, wherein the plurality of relieved channels extend generally parallel to an elongated axis of the rod.

10. The clamp assembly of claim 1, wherein the compressible ball and the second portion of the clamp assembly define a ball and socket joint such that the rod is permitted to pivot relative to the clamp assembly about a center of the ball.

* * * * *